United States Patent [19]

Sanderson et al.

[11] Patent Number: 4,705,903

[45] Date of Patent: Nov. 10, 1987

[54] CATALYTIC DECOMPOSITION OF IMPURITIES IN TERTIARY BUTYL ALCOHOL

[75] Inventors: John R. Sanderson, Leander; John M. Larkin, Austin, both of Tex.

[73] Assignee: Texaco Inc., White Plains, N.Y.

[21] Appl. No.: 932,822

[22] Filed: Nov. 20, 1986

[51] Int. Cl.$^4$ .................. C07C 29/88; C07C 29/132; C07C 31/12

[52] U.S. Cl. ........................................ 568/922; 44/56; 568/840

[58] Field of Search ........................... 568/922, 840 A

[56] References Cited

U.S. PATENT DOCUMENTS

| | | | |
|---|---|---|---|
| 2,854,487 | 9/1958 | Quin | 568/840 A |
| 2,993,072 | 7/1961 | Chiusoli | 568/840 A |
| 3,360,584 | 12/1967 | Kollar | 568/840 A |
| 3,624,165 | 11/1971 | Dehn et al. | 568/922 |
| 3,914,295 | 10/1975 | Rosenthal et al. | 568/840 A |
| 3,928,452 | 12/1975 | Brunie et al. | 568/840 A |
| 4,112,004 | 9/1978 | Mabuchi | 568/840 A |
| 4,123,616 | 10/1978 | Mabuchi et al. | 568/840 A |
| 4,219,685 | 8/1980 | Savine | 568/922 |
| 4,523,928 | 6/1985 | Hillman et al. | 568/922 |
| 4,547,598 | 10/1985 | Sanderson et al. | 568/922 |

*Primary Examiner*—J. E. Evans
*Attorney, Agent, or Firm*—Jack H. Park; Kenneth R. Priem; Carl G. Ries

[57] ABSTRACT

Motor-fuel grade tertiary butyl alcohol which is prepared, for example, by reacting propylene with tertiary butyl hydroperoxide to form propylene oxide and a tertiary butyl alcohol reaction product contaminated with residual amounts of tertiary butyl hydroperoxide and ditertiary butyl peroxide can be effectively catalytically treated under mild conversion conditions including a temperature of about 80° to 280° C. with a catalyst composed of iron, copper, chromia and cobalt, or the oxides thereof in order to substantially selectively convert the two peroxide contaminants to tertiary butyl alcohol and to thereby provide a treated tertiary butyl alcohol product substantially free from contaminating quantities of such peroxides.

6 Claims, No Drawings

CATALYTIC DECOMPOSITION OF IMPURITIES IN TERTIARY BUTYL ALCOHOL

BACKGROUND OF THE INVENTION

1. Field of the Invention

This invention relates to the catalytic purification of tertiary butyl alcohol prepared by the reaction of propylene with tertiary butyl hydroperoxide. More particularly, this invention relates to a method for the removal of residual contaminating quantities of tertiary butyl hydroperoxide and ditertiary butyl peroxide from a tertiary butyl alcohol feedstock which is prepared by the reaction of propylene with tertiary butyl hydroperoxide and is useful as an octaneenhancing component for motor fuels. In accordance with the present invention the peroxide-contaminated feedstock is brought into contact with a catalyst which is composed of iron, copper, chromia and cobalt in order to substantially selectively decompose both the tertiary butyl hydroperoxide and the ditertiary butyl peroxide to tertiary butyl alcohol.

2. Prior Art a. Process

A process for the manufacture of substituted epoxides from alpha olefins such as propylene is disclosed in Kollar U.S. Pat. No. 3,351,653 which teaches that an organic epoxide compound can be made by reacting an olefinically unsaturated compound with an organic hydroperoxide in the presence of a molybdenum, tungsten, titanium, columbium, tantalum, rhenium, selenium, chromium, zirconium, tellurium or uranium catalyst. When the olefin is propylene and the hydroperoxide is tertiary butyl hydroperoxide, propylene oxide and tertiary butyl alcohol are coproducts. U.S. Pat. No. 3,350,422 teaches a similar process using a soluble vanadium catalyst. Molybdenum is the preferred catalyst. A substantial excess of olefin relative to the hydroperoxide is taught as the normal procedure for the reaction. See also U.S. Pat. No. 3,526,645 which teaches the slow addition of organic hydroperoxide to an excess of olefin as preferred.

Stein, et al. in U.S. Pat. No. 3,849,451 have improved upon the Kollar process of U.S. Pat. Nos. 3,350,422 and 3,351,635 by requiring a close control of the reaction temperature, between 90°–200° C. and autogeneous pressures, among other parameters. Stein et al. also suggests the use of several reaction vessels with a somewhat higher temperature in the last vessel to ensure more complete reaction. The primary benefits are stated to be improved yields and reduced side reactions.

It is known that isobutane can be oxidized with molecular oxygen to form a corresponding tertiary butyl hydroperoxide and that the oxidation reaction can be promoted, for example with an oxidation catalyst (see Johnston U.S. Pat. No. 3,825,605 and Worrell U.S. Pat. No. 4,296,263.

Thus, tertiary butyl alcohol can be prepared either by the direct thermal or catalytic reduction of tertiary butyl hydroperoxide to tertiary butyl alcohol or by the catalytic reaction of propylene with tertiary butyl hydroperoxide to provide propylene oxide and tertiary butyl alcohol.

It is also known that tertiary butyl alcohol can be used as an octane-enhancing component when added to a motor fuel, such as gasoline. Thus, it has heretofore been proposed, as shown, for example, by Grane U.S. Pat. No. 3,474,151 to thermally decompose tertiary butyl hydroperoxide and ditertiary butyl peroxide to form tertiary butyl alcohol. The thermal decomposition must be conducted with care, as pointed out by Grane, in that tertiary butyl alcohol will start to dehydrate at a temperature of about 450° F. and in that the dehydration becomes rapid at temperatures above about 475° F. Moreover, the product from the thermal decomposition normally contains a minor amount of tertiary butyl hydroperoxide and ditertiary butyl peroxide which have an adverse effect upon the quality of motor fuels and must be substantially completely removed if the tertiary butyl alcohol is to be fully effective. Grane proposes to accomplish this thermally by heating tertiary butyl alcohol containing small quantities of such peroxides at a temperature of 375°–475° F. for a period of 1 to 10 minutes.

This concept was expanded upon by Grane et al. in U.S. Pat. Nos. 4,294,999 and 4,296,262 to provide integrated processes wherein, starting with isobutane, motor-fuel grade tertiary butyl alcohol was prepared by the oxidation of isobutane (e.g., in the presence of a solubilized molybdenum catalyst) to produce a mixture of tertiary butyl alcohol and tertiary butyl hydroperoxide from which a fraction rich in tertiary butyl hydroperoxide could be recovered by distillation. This stream, after being debutanized was subjected to thermal decomposition under pressure at a temperature of less than 300° F. for several hours to significantly reduce the concentration of the tertiary butyl hydroperoxide. However, the product of this thermal decomposition step still contained residual tertiary butyl hydroperoxide, most of which was thereafter removed by a final thermal treatment of the contaminated tertiary butyl hydroperoxide in the manner taught by Grane U.S. Pat. No. 3,474,151.

Thus, the removal of trace quantities of tertiary butyl hydroperoxide from motor grade tertiary butyl alcohol has received appreciable attention. However, little appears to have been published concerning the removal of trace quantities of ditertiary butyl peroxide, the more refractory of the two peroxides. This may be explainable both because ditertiary butyl peroxide is not always present in trace quantities in motor grade tertiary butyl alcohol (its presence or absence being a function of the reaction conditions used in oxidizing the isobutane starting material) and because, when present, it is present in significantly lower amounts. For example, after decomposition of the major amount of tertiary butyl hydroperoxide formed by the oxidation of isobutane, the tertiary butyl hydroperoxide residual content will normally be about 0.1 to about 1 wt. %, based on the tertiary butyl alcohol, while the residual ditertiary butyl peroxide content, if any, will only be about 0.1 to 0.5 wt. %.

Sanderson et al. U.S. Pat. No. 4,547,598 discloses the use of unsupported cobalt borate and cobalt borate supported on titanium dioxide to decompose organic hydroperoxides to alcohols. It has also been proposed to remove the residual hydroperoxide contaminants from tertiary butyl alcohol through the use of a heterogeneous cobalt oxide catalyst containing a copper oxide promoter as shown, for example, by Coile U.S. Pat. No. 4,059,598. Allison et al. in U.S. Pat. No. 3,505,360 have more generically taught that alkenyl hydroperoxides can be decomposed catalytically through the use of a catalyst based on a metal or compound of a metal of group IV-A, V-A or VI-A.

Other prior art patents relating to the production of hydroperoxides, but not with the problem of residual tertiary hydroperoxide contamination and tertiary butyl alcohol include patents such as Rust U.S. Pat. No. 2,383,919; Harvey U.S. Pat. No. 3,449,217; Poenisch et al. U.S. Pat. No. 3,778,382 and Williams et al. U.S. Pat. No. 3,816,548.

In West German DE No. 3248465-A a two-step process is disclosed wherein isobutane is oxidized noncatalytically with air to a conversion of about 48–90% to form the corresponding hydroperoxide, which is then catalytically decomposed under hydrogenation conditions in the presence of a supported catalyst such as palladium, platinum, copper, rhenium, ruthenium or nickel to form tertiary butyl alcohol. The decomposition product obtained using 1.3% palladium on lithium spinel as a catalyst contained significant quantities of acetone, water and methanol.

Mabuchi et al. U.S. Pat. No. 4,112,004 discloses a process for preparing monohydric or polyhydric alcohols from organic peroxides in the presence of a nickel catalyst by continuously feeding a solution of the organic peroxide (e.g., butadiene peroxide) and a suspension of the nickel catalyst to a reactor in a controlled ratio and continuously withdrawing reaction mixture at a rate adequate to maintain a constant weight and composition of the reaction mixture in the reactor.

In U.S. Pat. No. 4,123,616 to Mabuchi et al. a process is disclosed for hydrogenating an organic peroxide to the corresponding mono- or polyhydric alcohol in a suspension or fluidized bed process under hydrogen pressure in the presence of a nickel catalyst. Examples are given showing the conversion of butadiene peroxide to 1,4-butane diol and 1,2-butane diol and the conversion of tertiary butyl hydroperoxide to tertiary butyl alcohol.

b. Catalysts

Godfrey U.S. Pat. No. 3,037,025 discloses the preparation of N-alkyl substituted piperazines using catalyst compositions consisting of the metals and oxides of copper, nickel and cobalt (including mixtures thereof) which may also be promoted by the inclusion of a normally non-reducible metal oxide such as chromium, aluminum, iron, calcium, magnesium, manganese and the rare earths. Preferred catalyst compositions are indicated as containing from about 44 to about 74 wt. % of nickel, about 5 to about 55 wt. % of copper and about 1 to about 5 wt. % of chromia.

Moss U.S. Pat. No. 3,151,112 discloses catalyst compositions useful for the preparation of morpholines including one or more metals from the group including copper, nickel, cobalt, chromium, molybdenum, manganese, platinum, palladium and rhodium, which may also be promoted with normally nonreducible oxides such as chromium oxide, molybdenum oxide and manganese oxide. Representative catalyst compositions include those containing from about 60 to about 85 wt. % of nickel, about 14 to about 37 wt. % of copper and about 1 to about 5 wt. % of chromia. Nickel, copper, chromia catalysts are also disclosed in Moss U.S. Pat. No. 3,151,115 and Moss U.S. Pat. No. 3,152,998.

Winderl et al. U.S. Pat. No. 3,270,059 teaches the use of catalysts containing a metal of groups I-B and VIII of the Periodic System. Examples of suitable catalysts are stated to be copper, silver, iron, nickel, and particularly, cobalt.

Boettger et al. U.S. Pat. No. 4,014,933 discloses catalysts containing cobalt and nickel promoted with copper such as those containing from about 70 to about 95 wt. % of a mixture of cobalt and nickel and from about 5 to about 30 wt. % of copper.

Habermann U.S. Pat. No. 4,152,353 discloses catalyst compositions comprising nickel, copper and a third component which may be iron, zinc, zirconium or a mixture thereof such as catalysts containing from about 20 to about 49 wt. % of nickel, about 36 to about 79 wt. % of copper and about 1 to about 15 wt. % of iron, zinc, zirconium or a mixture thereof. Similar catalyst compositions are mentioned in Habermann U.S. Pat. No. 4,153,581.

European patent application No. 0017651 filed Oct. 20, 1980, contains a disclosure of catalyst compositions related to those disclosed by Habermann, such catalyst compositions being composed of nickel or cobalt, copper and iron, and zinc or zirconium such as compositions containing 20 to 90% cobalt, 3 to 72% copper and 1 to 16% of iron, zinc or zirconium and catalyst compositions containing 20 to 49% nickel, 36 to 79% copper and 1 to 16% of iron, zinc or zirconium.

German Offen. No. 2,721,033 discloses a catalyst composition containing 35% nickel, about 87.5% iron and a minor amount of chromia.

Johansson et al. U.S. Pat. No. 3,766,184 discloses catalyst compositions composed of iron and nickel and/or cobalt.

Grane et al. in their U.S. Pat. Nos. 4,294,999 and 4,296,262 teach the removal of contaminating quantities of tertiary butyl hydroperoxide and ditertiary butyl peroxide by a short high temperature thermal treatment. However, thermal composition in this manner normally results in the formation of oxygenated products such as acetone and methanol, which are also deliterous to the quality of the final tertiary butyl alcohol motor fuel product.

Copending Sanderson et al. U.S. patent application Ser. No. 06/879,660 filed June 27, 1986, and entitled "Catalytic Purification of Tertiary Butyl Alcohol" discloses a process for purifying tertiary butyl alcohol wherein tertiary butyl hydroperoxide and ditertiary butyl peroxide impurities contained therein are selectively reduced in the presence of a specially proportioned nickel, copper, chromia, iron oxide catalyst.

BACKGROUND

When isobutane is reacted with molecular oxygen the principal products of the reaction are tertiary butyl alcohol and tertiary butyl hydroperoxide. However, minor amounts of other peroxides, including ditertiary butyl peroxide are also formed. Generally speaking, from about 10 to about 100 parts of tertiary butyl hydroperoxide are formed per part of ditertiary butyl peroxide. Minor quantities of other contaminants are also formed.

A listing of the components present in a representative reaction product, and their nominal boiling points is given in Table A.

TABLE A

| Component | NBP (°C.) |
|---|---|
| Isobutane | −11.7 |
| Methyl formate | 31.8 |
| Acetone | 56.3 |
| Isobutylene oxide | 60.0 |
| Isobutyraldehyde | 64.1 |
| Methanol | 64.7 |
| Methyl-t-butyl peroxide | 74.2 |
| Isopropyl alcohol | 82.3 |

TABLE A-continued

| Component | NBP (°C.) |
|---|---|
| Tertiary butyl alcohol | 82.4 |
| Ditertiary butyl peroxide | 111.0 |
| t-butyl-i-pr-peroxide | 124.0 |
| Tertiary butyl formate | 163.8 |

The minor by-products are sometimes difficult to remove. For example, tertiary butyl formate has a higher boiling point than ditertiary butyl hydroperoxide but tends to distill overhead, which suggests that it forms a minimum boiling azeotrope with another component or components.

Tertiary butyl hydroperoxide is useful as a raw material for the manufacture of tertiary butyl alcohol either by catalytic decomposition of the tertiary butyl hydroperoxide in the presence of a molybdenum catalyst as taught in Grane et al. U.S. Pat. No. 4,249,999 and for 4,296,262 or Worrell U.S. Pat. No. 4,296,263, or by the catalytic reaction of tertiary butyl hydroperoxide with an olefin such as propylene to form an epoxide and tertiary butyl alcohol.

When the olefin is propylene, the coproduct is propylene oxide. The reaction conditions used for the conversion of tertiary butyl hydroperoxide, by either process, to tertiary butyl alcohol are such that the ditertiary butyl peroxide normally is not consumed or destroyed and remains in the reaction mixture as an impurity. Only a minor amount of the peroxidation reaction mixture formed by the reaction of molecular oxygen with isobutane will be composed of ditertiary butyl peroxide. However, this minor amount may constitute as much as about 0.5 wt. % of the total peroxidation reaction mixture.

For example, when tertiary butyl hydroperoxide is recovered from the peroxidation reaction mixture obtained by the reaction of molecular oxygen with isobutane, the ditertiary butyl peroxide will also normally be present as a contaminant. Therefore, when the tertiary butyl hydroperoxide is reacted with propylene to form propylene oxide and tertiary butyl alcohol, the ditertiary butyl peroxide will be present in the reaction mixture and in the reaction product.

The product of the reaction of tertiary butyl hydroperoxide with propylene is normally separated into useful components, usually by distillation, to form, for example, sequential distillate fractions composed of unreacted propylene, propylene oxide and tertiary butyl alcohol. The ditertiary butyl hydroperoxide will normally be present in the recovered tertiary butyl alcohol as a contaminant together with other contaminants such as residual tertiary butyl hydroperoxide, acetone, methyl formate, methanol, tertiary butyl formate, isopropyl alcohol, etc.

A tertiary butyl alcohol product prepared by either of the processes described above, and contaminated with minor amounts of tertiary butyl hydroperoxide and ditertiary butyl peroxide may be used as a feedstock for the present invention.

Tertiary butyl hydroperoxide can decompose thermally and/or catalytically to form acetone. Tertiary butyl alcohol can be decomposed to form water and isobutylene. Accordingly, the tertiary butyl alcohol feedstock of the present invention is not entirely satisfactory for use as an octaneenhancing component for motor fuels, such as gasoline, in that tertiary butyl alcohol will normally be considered unsatisfactory for motor fuel use if it contains more than about 3 wt. % of acetone, more than about 1 wt. % of isobutylene, more than about 100 ppm of ditertiary butyl peroxide and more than 100 ppm of tertiary butyl hydroperoxide. Desirably, the tertiary butyl alcohol will contain about 1 wt. % or less of acetone, 0.5 wt. % or less of isobutylene and 10 ppm or less of ditertiary butyl peroxide and 100 ppm or less of tertiary butyl hydroperoxide.

SUMMARY OF INVENTION

It has been surprisingly discovered in accordance with the present invention that motor-fuel grade tertiary butyl alcohol which is contaminated with residual amounts of ditertiary butyl peroxide and tertiary butyl hydroperoxide can be effectively catalytically treated with a catalyst composed of iron, copper, chromia and cobalt under mild catalytic conditions including a temperature of about 80° to 220° C. at a pressure sufficient to maintain a liquid phase reaction mixture (normally, about 200 to 800 psig., depending on reaction temperature). Higher pressures of up to about 2000 psig. can be used, if desired, but there is no particular advantage in using the higher pressures. This treatment will substantially selectively convert the peroxide contaminants to tertiary butyl alcohol and thereby provide a treated product substantially free of contaminating quantities of tertiary butyl hydroperoxide and ditertiary butyl peroxide. Thus, the formation of unwanted isobutylene and oxygenated derivatives of the peroxide contaminates, including acetone and methanol is substantially avoided.

The results obtained with the process of the present invention are surprising and unexpected in several respects. Catalytic or thermal decomposition of tertiary butyl hydroperoxide and ditertiary butyl peroxide normally results in the formation of acetone as the favored decomposition product. Thus, the favorable effect on the quality of motor fuel grade tertiary butyl alcohol that is obtained by the substantially complete elimination of the two peroxides will be largely counterbalanced if the decomposition product is principally acetone.

Another problem is encountered in the catalytic decomposition of the residual tertiary butyl hydroperoxide and ditertiary butyl peroxide contaminants present in the tertiary butyl alcohol in that the catalyst may also catalyze the dehydration of tertiary butyl alcohol to isobutylene. Isobutylene is also an undesired contaminant, even when only trace quantities are present.

Moreover, we have found that catalysts that are effective for the substantially complete decomposition of tertiary butyl hydroperoxide are normally only partially effective, at best, for the catalytic decomposition of ditertiary butyl peroxide.

Thus, the provision of the process of the present invention wherein a motor-fuel grade tertiary butyl alcohol feedstock containing contaminating quantities of both ditertiary butyl peroxide and tertiary butyl hydroperoxide, is catalytically treated for the decomposition of the peroxides so that they are substantially completely removed without significantly adding to the level of contamination due to the formation of acetone, methanol and isobutylene constitutes a distinct advantage over the prior art.

STARTING MATERIALS

The starting materials for the process of the present invention include a motor-fuel grade tertiary butyl alcohol feedstock obtained in the manner described above by the reaction of propylene with tertiary butyl hydroperoxide to form propylene oxide and tertiary butyl alcohol by the oxidation of isobutane to form tertiary butyl hydroperoxide, etc.

The motor-fuel grade tertiary butyl alcohol feedstock obtained by the reaction of propylene with tertiary butyl hydroperoxide to form propylene oxide and tertiary butyl alcohol will contain contaminating quantities of teritary butyl hydroperoxide, ditertiary butyl peroxide, and acetone, and may also contain contaminating quantities of methanol and isobutylene. The normal levels of contamination of such materials are such that the tertiary butyl alcohol will normally contain, prior to treatment, from about 0.1 to about 5 wt. % of tertiary butyl hydroperoxide and from about 0.1 to about 5 wt. % of ditertiary butyl peroxide. Minor quantities of other contaminants may also be present.

As indicated earlier, the reaction conditions used in the catalytic oxidation of isobutane will sometimes result in the formation of ditertiary butyl peroxide. Thus, the feedstock to be used for the practice of the present invention is an impure motor grade tertiary butyl alcohol containing from about 0.1 to about 5 wt. % of tertiary butyl hydroperoxide and from about 0.1 to about 5 wt. % of ditertiary butyl peroxide.

The catalyst compositions of the present invention consist essentially of the oxides of and/or metallic iron, copper, chromia and cobalt in the proportions (on an oxygenfree basis) of about 20 to about 80 wt. % of iron, about 5 to about 40 wt. % of copper, about 0.1 to about 10 wt. % of chromia and about 0.01 to 5 wt. % of cobalt.

More preferably, the catalyst compositions of the present invention will contain about 30 to about 50 wt. % of iron and about 10 to about 30 wt. % of copper, about 1 to about 5 wt. % of chromia and about 0.5 to about 2 wt. % of cobalt.

As indicated, the catalyst compositions of the present invention may be composed of one or more of the oxides of iron, copper, chromium and cobalt in the proportions (calculated on an oxygen-free basis) given above.

The catalyst may also be supported on a suitable inert support such as alumina, silica, titania, etc.

Although the catalyst compositions of the present invention may be utilized in powdered form in conducting batch reactions, their utility is enhanced when they are used in pelleted form for catalyzing the reaction in a continuous process. When a catalyst is used in pelleted form for a continuous reaction, it is necessary that the pellets have good physical and chemical properties so that they will not disintegrate or break during the course of the continuous peroxide decomposition. The catalyst compositions of the present invention have such properties.

Catalytic Treatment of Tertiary Butyl Alcohol

In accordance with the present invention, a tertiary butyl alcohol feedstock, as above described, is brought into contact with a catalyst of the present invention under reaction conditions correlated to substantially selectively catalytically convert both the tertiary butyl hydroperoxide and ditertiary butyl peroxide contaminants in the tertiary butyl alcohol feedstock to tertiary butyl alcohol with not more than a minor increase in the level of contamination of the acetone, methanol and isobutylene also normally present in the tertiary butyl alcohol as contaminants.

The reaction may be conducted batchwise in an autoclave using powdered catalyst or may be conducted on a continuous basis by passing the tertiary butyl alcohol through a reactor containing a bed of a catalyst of the present invention under reaction conditions including a temperature within the range of about 80° to about 280° C. and, more preferably, from about 110° to about 180° C. The reaction is preferably conducted at 200 to 800 psig., although higher pressures of up to about 2000 psig. may be used if desired. When the reaction is conducted batchwise, contact time may suitably be from about 0.5 to about 4 hours. When the reaction is conducted on a continuous basis, the tertiary butyl alcohol should be passed over the bed of catalyst at a liquid hourly space velocity of about 0.25 to about 5.

The reaction product, after being degassed, is suitable for use as an octane-enhancing component of motor fuel, such as gasoline.

Thus, for example, the effluent from the reactor may be passed through a phase separation zone in order to permit gaseous reaction components including hydrogen and isobutane to volatilize from the product to thereby provide the desired reaction product.

The specific correlation of conditions to be utilized with any specific catalyst of the present invention can be determined by one of ordinary skill in the art with comparative ease. Thus, for example, the tertiary butyl alcohol feedstock should be analyzed prior to catalytic treatment to determine the level of contamination by tertiary butyl hydro peroxide, ditertiary butyl peroxide, acetone, methanol and isobutylene. If there is an insufficient decomposition of the hydroperoxides such that a significant amount (e.g., more than about 0.1 wt. %) of tertiary butyl hydroperoxide and/or ditertiary butyl peroxide is still present, the reaction conditions are not sufficiently severe, and should be increased such as, for example, by increasing reaction temperature or contact time in order to obtain the desired decomposition of the tertiary butyl hydroperoxide.

If, on the other hand, there is a significant increase in the level of contamination of acetone, isobutylene and/or methanol, the reaction conditions are too severe for the particular catalyst and the reaction conditions should be ameliorated (e.g., by reducing contact time or temperature).

WORKING EXAMPLES

Example A

Catalyst Preparation

Catalyst BBB 6098-76 - Preparation of Ni/Cu/Cr/Mo Catalyst

A solution of 2856 g of $H_2O$, 1530 g of $Ni(NO_3)_2.6H_2O$, 285.6 g of hydrated $Cu(NO_3)_2$, and 96.9 g of $Cr(NO_3)_3.9H_2O$ at 80° C., and a solution of 2400 ml $H_2O$, 713 g of $Na_2CO_3$, 12.0 g of NaOH and 60.0 g of ammonium molybdate at 80° C. were added simultaneously to 1000 ml of rapidly stirred water at 80° C. over a 2¼ hour period at rates such that the pH remained near 7.0. The mixture was filtered hot. The filter cake was stirred with 2500 ml of $H_2O$ at 80° C. and filtered hot. This procedure was repeated five more times. The filter cake was dried at 135° C. for one day and at 90° C. for two mor days. Anal.:40.8% Ni, 10.6% Cu, 1.7% Cr, 4.7% Mo, and 40 ppm Na.

The powder was calcined at 400° C. for four hours. Anal.:51.5% Ni, 12.8% Cu, 1.7% Cr, 5.8% Mo, 88 ppm Na.

The calcined material was reduced in flowing $N_2/H_2$ and finally all $H_2$ at 335°–362° C. over a six day period. It was stabilized at room temperature in flowing $N_2$/air and finally all air. Yield=457.54 g. Anal.:60.5% Ni, 15.4% Cu, 1.8% Cr, 7.0% Mo, 180 ppm Na.

Graphite (3.0 wt. %) was added, and the catalyst powder was made into ⅛"×⅛" tablets (260 cc) of 15–25 lb crush strength.

Catalyst AAA 6098-40 - Preparation of Fe/Cu/Cr/Co Catalyst

A solution containing 3200 ml of $H_2O$, 1979.7 g (4.9 moles) of $Fe(NO_3)_3.9H_2O$, 413.9 g (approx. 1.4 moles) of hydrated $Cu(NO_3)_2$, 160.1 g (0.4 moles) of $Cr(NO_3)_3.9H_2O$, and 29.1g (0.1 moles) of $Co(NO_3)_2.6H_2O$ at 80° C., and a solution containing 3220 ml of $H_2O$ and 1080.7 g (10.20 moles) of $Na_2CO_3$ at 80° C. were added simultaneously to 1000 ml of rapidly stirred water at rates such that the pH of the resultant solution remained approximately 7. The addition required 1 hr. and 55 minutes. After an additional half-hour of stirring at 80°–83° C., the mixture was filtered. The filter cake was stirred with 3000 ml of $H_2O$ at 80° C. and refiltered. This operation was repeated five more times. The final filter cake was dried at 145° C. for approximately 18 hours. Anal.:44.4% Fe, 19.0% Cu, 3.6% Cr, and 0.72% Co.

The powdered carbonates were calcined at 450° C. for five hours. Anal.: 43.2% Fe, 18.1% Cu, 3.5% Cr, and 0.82% Co.

The calcined powder was reduced at 350° C. for 21 hours in a hydrogen stream after prior exposure to flowing $N_2H_2$ mixtures at 350° C. Final reduction was in flowing hydrogen at 390°–395° C. for 1¾ hours. The powder was cooled and a mixture of flowing $N_2$/air and finally all air was introduced at 10°–22° C. Anal.:49.5% Fe, 21.5% Cu, 4.2% Cr and 0.95% Co.

The reduced and stabilized catalyst was ground to −80 mesh particles, mixed with 3% graphite, and formed into ⅛"×⅛" tablets of about 42 lb average crush strength.

I. Equipment and Procedures

In all cases, these evaluations were performed in a 100 cc reactor constructed of ½ inch stainless steel tubing 17 inches long connected to a ¼ inch feed and effluent lines with swagelok fittings. The reactor tube was situated inside of a 3×3 inch aluminum block which was heated electrically with four 1000 watt strip heaters. Temperature control was achieved with a Thermoelectric controller monitoring thermocouples attached to the skin of the reactor body. The feed was charged to the reactor system with a Beckman 110 A.L.C. pump. The reactor effluent was collected in a glass jug and sampled after the system and lined-out at the prescribed temperature for at least 2.5 hours.

The catalysts that were used in initial comparative working examples are listed in Table I together with a brief description of their composition.

TABLE I

| Code | Catalysts for Peroxide Decomposition<br>Catalyst Description |
|------|--------------------------------------------------------------|
| AA   | 25% Cobalt on a proprietary silica-alumina support, ⅛" extrusions |
| BB   | Unsupported manganese catalyst, ⅛" tablets |
| CC   | 19% W, 6% Ni on silica support, 3/16" extrusions |
| DD   | 10% $V_2O_5$ on a silica-alumina support, 3/16" extrusions |
| EE   | Unsupported 55% Mo and 11% Fe, ⅛" tablets (As moles of metals and metal oxides) |
| FF   | Copper Chromite (79% CuO, 17% $Cr_2O_3$), ⅛" tablets |
| GG   | Ni 30.7%, Cu 12.6%, Fe 3.3%, Cr 0.64% (as moles of metals and metal oxides) |
| AAA  | 49.5% Fe, 21.5% Cu, 4.2% Cr, 0.95% Co |
| BBB  | 60.5% Ni, 15.4% Cu, 1.8% Cr, 7.0% Mo |

Example 1-A

In a first series of experiments a simulated tertiary butyl alcohol feedstock having the contamination levels listed for notebook No. 5787-76-1 in Table II was used as the feedstock.

In run 6064-60-1, the feedstock was heated in the reactor at a temperture of about 160° C. and a pressure of about 520 psig., being passed to the reactor at the rate of about 0.9 lbs/hr. As will be noted from Table II, there was a significant reduction in the level of tertiary butyl hydroperoxide contamination, but only a minor decrease in the level of contamination due to ditertiary butyl peroxide. Note also there was a significant increase in the level of contamination due to the formation of acetone.

The next series of sets of runs were made using the catalysts, as identified in Table I, under the reaction conditions noted in Table II with the results that are also there noted. This series of tests was, essentially, a screening test involving a wide variety of commercially available catalyst together with catalysts prepared in our laboratories. Thus, the catalysts included a supported cobalt catalyst (catalyst AA), a manganese catalyst (catalyst BB), a tungsten catalyst (catalyst CC), a vanadia catalyst (catalyst DD), a molybdena catalyst (catalyst EE), a copper chromite catalyst (catalysts FF) and a nickel, copper, iron, chromia catalyst (catalyst GG).

TABLE II

| | | | | Catalytic Decomposition of Peroxides in tert-Butyl Alcohol | | | | | | |
|---|---|---|---|---|---|---|---|---|---|---|
| N.B. Number | Cat. Code | Temp. (°C.) | Feed #/Hr | Pressure (psig) | $H_2O$ (wt. %) | TBHP (ppm) | Products by GC Analysis, Wt. % | | | |
| | | | | | | | DTBP | Acetone | MeOH | IB= |
| 5787-76-1 | — | — | (Feed) | — | 1.7 | 1555 | 0.117 | 0.002 | 0.003 | ~0 |
| 6064-60-1 | None | 160 | 0.90 | 520 | 1.8 | 227 | 0.095 | 0.033 | 0.002 | ~0 |
| 6064-77-1 | AA | 80 | 1.04 | 500 | 1.7 | 113 | 0.118 | 0.010 | ~0 | ~0 |
| -2 | | 120 | 0.99 | 500 | 1.7 | 6.13 | 0.118 | 0.016 | 0.001 | 0.00077 |
| -3 | | 160 | 1.00 | 500 | 1.7 | 4.76 | 0.100 | 0.033 | 0.002 | 0.010 |
| 6064-82-1 | BB | 80 | 1.02 | 500 | 1.77 | 113 | 0.116 | 0.010 | ~0 | ~0 |
| -2 | | 120 | 1.00 | 500 | 1.74 | 10.99 | 0.116 | 0.017 | ~0 | ~0 |
| -3 | | 160 | 1.00 | 500 | 1.72 | 3.71 | 0.102 | 0.036 | 0.001 | 0.00097 |
| 6064-84-1 | CC | 120 | 0.99 | 500 | 1.74 | 238 | 0.107 | 0.002 | ~0 | 0.003 |
| -2 | | 80 | 1.02 | 500 | 1.72 | 162 | 0.116 | 0.00097 | ~0 | ~0 |
| -3 | | 160 | 1.00 | 500 | 1.90 | 201 | 0.101 | 0.020 | 0.001 | 0.331 |

TABLE II-continued

Catalytic Decomposition of Peroxides in tert-Butyl Alcohol

| N.B. Number | Cat. Code | Temp. (°C.) | Feed #/Hr | Pressure (psig) | H₂O (wt. %) | TBHP (ppm) | Products by GC Analysis, Wt. % | | | |
|---|---|---|---|---|---|---|---|---|---|---|
| | | | | | | | DTBP | Acetone | MeOH | IB= |
| 6064-87-1 | DD | 80 | 0.99 | 500 | 2.7 | 692 | 0.117 | 0.004 | 0.002 | 0.284 |
| -2 | | 120 | 0.96 | 500 | 3.9 | 178 | 0.121 | 0.019 | 0.003 | 2.330 |
| -3 | | 160 | 0.95 | 500 | 8.8 | 12.73 | 0.111 | 0.044 | 0.002 | 3.853 |
| 6064-90-1 | EE | 80 | 0.91 | 500 | 1.7 | 563 | 0.119 | 0.003 | 0.002 | 0.029 |
| -2 | | 120 | 1.00 | 500 | 2.2 | 488 | 0.119 | 0.003 | 0.002 | 1.021 |
| -3 | | 160 | 1.02 | 500 | 6.6 | 136 | 0.116 | 0.026 | 0.001 | 4.588 |
| 6064-92-1 | FF | 80 | 1.02 | 500 | 1.7 | 282 | 0.116 | 0.004 | 0.002 | 0.003 |
| -2 | | 120 | 0.99 | 500 | 1.7 | 184 | 0.115 | 0.012 | 0.004 | 0.001 |
| -3 | | 160 | 1.00 | 500 | 1.8 | 15.8 | 0.102 | 0.051 | 0.006 | 0.011 |
| 6064-93-1 | GG | 80 | 1.02 | 500 | 1.7 | 195 | 0.102 | 0.007 | 0.004 | 0.005 |
| -2 | | 120 | 1.00 | 500 | 1.7 | 12.5 | 0.089 | 0.009 | 0.004 | 0.002 |
| -3 | | 160 | 1.00 | 500 | 1.7 | 8.48 | 0.032 | 0.051 | 0.004 | 0.038 |
| 6089-6-1 | GG | 160 | 1.04 | 500 | 1.71 | 22.1 | 0.026 | 0.044 | 0.004 | 0.045 |
| -2 | | 200 | 1.02 | 500 | 2.03 | 21.6 | 0.008 | 0.266 | ~0 | 0.575 |
| -3 | | 240 | 1.02 | 500 | 4.68 | 10.6 | 0.004 | 0.302 | 0.001 | 3.366 |
| 6089-7-1 | GG | 160 | 0.21 | 500 | 1.97 | 25.5 | 0.012 | 0.165 | 0.002 | 0.159 |
| -2 | | 200 | 0.25 | 500 | 2.23 | 22.1 | 0.003 | 0.246 | ~0 | 1.909 |
| -3 | | 240 | 0.28 | 500 | — | 14.0 | 0.003 | 0.511 | ~0 | 1.934 |
| 6089-12-1 | GG | 140 | 0.23 | 500 | 2.15 | 20.7 | 0.014 | 0.097 | 0.003 | 0.321 |
| -2 | | 180 | 0.22 | 500 | 4.08 | 22.5 | 0.006 | 0.240 | ~0 | 3.319 |

Turning now to Table II, it will be noted that in all instances there was a reduction in the level of contamination of tertiary butyl hydroperoxide. However, in certain runs (e.g., 6064-84-1, 6064-87-1, 6064-90-1 and 6064-90-2) the contamination level was greater than the level accomplished by straight thermal decomposition at 160° C. in run 6064-60-1.

Insofar as the reduction of the level of ditertiary butyl peroxide is concerned, the only catalyst that reduced the level of ditertiary butyl peroxide below that obtainable by straight thermal decomposition (run 6064-60-1) was catalyst GG.

In view of the favorable results obtained at the higher temperature with catalyst GG, three additional runs were made scanning a higher bracket of temperatures ranging from 140°–240° C. Note from run 6089-6, triplicate runs 6089-7 and duplicate runs 6089-12 that in all instances a very low level of contamination of ditertiary butyl peroxide was achieved. However, when the temperature was more than about 160° C. an unacceptable level of isobutylene contamination was obtained. This is shown by run 6089-6-1, 6089-6-2 and 6089-6-3. Longer contact times still further reduced the level of contamination of ditertiary butyl peroxide but resulted in unacceptably high levels of isobutylene contamination as shown by triplicate runs 6089-7 and duplicate runs 6089-12.

Example 1-B

A series of tests were conducted using a catalyst composition of the present invention together with a reference catalyst of closely related composition. For this series of tests, however, tertiary butyl hydroperoxide was eliminated from the simulated feedstock because it had already been demonstrated that a catalyst which is effective for reducing the level of contamination of ditertiary butyl peroxide will also be effective for reducing the level of contamination of tertiary butyl hydroperoxide. The catalysts tested and the results obtained are summarized in Table III.

TABLE III

Catalytic Decomposition of DTBP in tert-Butyl Alcohol

| N.B. Number | Cat. Code | Temp. (°C.) | Feed #/Hr | Pressure (psig) | H₂O (wt. %) | Products by GC Analysis, Wt. % | | | |
|---|---|---|---|---|---|---|---|---|---|
| | | | | | | DTBP | Acetone | MeOH | IB= |
| 6123-2-2 | — | — | (Feed) | — | 0.05 | 0.841 | ~0 | ~0 | 0.003 |
| 6150-25-1 | AAA | 130 | 0.2 | 500 | 0.11 | 0.005 | 0.153 | 0.003 | 0.017 |
| -2 | | 140 | 0.2 | 500 | 0.17 | 0.005 | 0.233 | 0.005 | 0.029 |
| -3 | | 150 | 0.2 | 500 | 0.20 | 0.006 | 0.260 | 0.007 | 0.038 |
| -4 | | 160 | 0.2 | 500 | 0.32 | 0.006 | ~0 | ~0 | 0.111 |
| 6150-26-1 | | 130 | 1.0 | 500 | 0.12 | 0.390 | 0.090 | ~0 | 0.007 |
| -2 | | 140 | 1.0 | 500 | 0.11 | 0.254 | 0.137 | ~0 | 0.011 |
| -3 | | 150 | 1.0 | 500 | 0.11 | 0.130 | 0.185 | 0.004 | 0.013 |
| -4 | | 160 | 1.0 | 500 | 0.16 | 0.063 | 0.223 | 0.003 | 0.020 |
| 6150-27-1 | | 170 | 1.0 | 500 | 0.17 | 0.039 | 0.263 | 0.005 | 0.023 |
| -2 | | 180 | 1.0 | 500 | 0.20 | 0.014 | 0.294 | 0.007 | 0.027 |
| -3 | | 190 | 1.0 | 500 | 0.17 | 0.003 | 0.327 | 0.008 | 0.031 |
| -4 | | 200 | 1.0 | 500 | 0.17 | 0.011 | 0.307 | 0.011 | 0.026 |
| 6150-28-1 | BBB | 130 | 0.2 | 500 | 0.18 | 0.063 | 0.125 | 0.017 | 0.037 |
| -2 | | 140 | 0.2 | 500 | 0.33 | 0.009 | 0.133 | 0.021 | 0.023 |
| -3 | | 150 | 0.2 | 500 | 0.28 | 0.007 | 0.201 | 0.025 | 0.175 |
| 6150-29-1 | | 130 | 1.0 | 500 | 0.19 | 0.774 | 0.033 | ~0 | 0.012 |
| -2 | | 140 | 1.0 | 500 | 0.20 | 0.699 | 0.066 | 0.012 | 0.012 |
| -3 | | 150 | 1.0 | 500 | 0.18 | 0.429 | 0.123 | 0.017 | 0.017 |
| -4 | | 160 | 1.0 | 500 | 0.17 | 0.211 | 0.182 | 0.022 | 0.022 |
| 6150-30-1 | | 170 | 1.0 | 500 | 0.18 | 0.077 | 0.244 | 0.029 | 0.031 |
| -2 | | 180 | 1.0 | 500 | 0.25 | 0.014 | 0.264 | 0.029 | 0.034 |
| -3 | | 190 | 1.0 | 500 | 0.28 | 0.005 | 0.397 | 0.029 | 0.082 |

TABLE III-continued
Catalytic Decomposition of DTBP in tert-Butyl Alcohol

| N.B. Number | Cat. Code | Temp. (°C.) | Feed #/Hr | Pressure (psig) | H₂O (wt. %) | Products by GC Analysis, Wt. % | | | |
|---|---|---|---|---|---|---|---|---|---|
| | | | | | | DTBP | Acetone | MeOH | IB= |
| -4 | | 200 | 1.0 | 500 | 0.38 | 0.006 | 0.362 | 0.028 | 0.188 |

AAA = 49.5% Fe, 21.5% Cu, 4.2% Cr, 0.95% Co
BBB = 60.5% Ni, 15.4% Cu, 1.8% Cr, 7.0% Mo

Note from the results reported in Table III that catalyst AAA of the present invention significantly reduced the contamination level of ditertiary butyl peroxide (DTBP) to consistently lower levels of contamination than those obtained with reference catalyst BBB. Also note the very low isobutylene contamination level obtained with catalyst AAA as compared with catalyst BBB. Compare experiment 6150-28-4 conducted with the catalyst of the present invention which was conducted at 200° C., 500 psig. and a liquid feed rate of 1.0 lb/hr with 6150-30-4 conducted with the reference catalyst under the same conditions. The catalyst of the present invention gives only 0.026% isobutylene, whereas the reference catalyst gives 0.188% isobutylene. Thus, the catalyst of the present invention gives only 0.30% acetone whereas the reference catalyst gives 0.362% acetone.

It is also significant to note that although some of the catalysts in Table II gave low yields of isobutylene, none of the catalysts in Table II was as effective as the catalyst of the present invention insofar as the thermal decomposition of ditertiary butyl peroxide is concerned. Note from Table III that significantly lower levels of ditertiary butyl peroxide were obtained in the product as compared with the amount of ditertiary butyl peroxide present in the product of the examples of Table II.

The foregoing examples are given by way of illustration only, and are not intended as limitations on the scope of this invention, as defined by the appended claims.

Having thus described our invention, what is claimed is:

1. A method for enhancing the motor fuel quality of a tertiary butyl alcohol feedstock contaminated with residual quantities of tertiary butyl hydroperoxide and ditertiary butyl peroxide, which comprises the steps of:
   a. contacting said feedstock in a reaction zone with a catalyst at a temperature of about 80° to about 220° C. for a period of time sufficient to substantially selectively decompose said tertiary butyl hydroperoxide and said ditertiary butyl peroxide to tertiary butyl alcohol, and
   b. recovering substantially hydroperoxide-free tertiary butyl alcohol from the products of said reaction,
   c. said catalyst being composed of a metals component consisting essentially of metallic iron, copper, chromium and cobalt or the oxides of one or more of said metals in the proportions, on an oxygen-free basis, of about 20 to about 80 wt. % of iron and about 5 to about 40 wt. % of copper from about 0.1 to about 10 wt. % of chromium and from about 0.01 to about 5 wt. % of cobalt.

2. A method as in claim 1 wherein reaction is conducted at a temperature of about 110° to about 180° C.

3. A method for enhancing the motor fuel quality of a tertiary butyl alcohol feedstock obtained by the reaction of propylene with tertiary butyl hydroperoxide to form propylene oxide and said tertiary butyl alcohol feedstock, said tertiary butyl alcohol feedstock being contaminated with residual quantities of tertiary butyl hydroperoxide, ditertiary butyl peroxide, acetone, methanol and isobutylene said method comprising the steps of:
   a. contacting said feedstock in a reaction zone with a catalyst at a temperature of about 80° to about 160° C. for a period of time sufficient to substantially selectively decompose said tertiary butyl hydroperoxide and said ditertiary butyl peroxide to tertiary butyl alcohol, and
   b. recovering from the products of said reaction, product tertiary butyl alcohol containing not more than about 100 of tertiary butyl hydroperoxide, not more than about 100 ppm of ditertiary butyl peroxide, not more than about 3 wt. % of acetone and not more than about 0.5 wt. % of isobutylene,
   c. said catalyst being composed of a metals component consisting essentially of metallic iron, copper, chromium and cobalt or the oxides of one or more of said metals in the proportions, on an oxygen-free basis, of about 20 to about 80 wt. % of iron, about 5 to about 40 wt. % of copper, about 0.1 to about 10 wt. % of chromium and from about 0.01 to about 5 wt. % of cobalt.

4. A method as in claim 3 wherein the catalyst contains about 30 to about 50 wt. % of iron, about 10 to about 30 wt. % of copper, about 1 to about 5 wt. % of chromia and from about 0.01 to about 5 wt. % of cobalt.

5. A method as in claim 3 wherein the catalyst contains about 49.5 wt. % of iron, about 21.5 wt. % of copper, about 4.2 wt. % of chromium and about 0.95 wt. % of cobalt.

6. A method as in claim 3 wherein the product tertiary butyl alcohol contains not more than about 10 ppm of tertiary butyl hydroperoxide, not more than about 100 ppm of ditertiary butyl peroxide, not more than about 1 wt. % of acetone and not more than about 0.5 wt. % of isobutylene.

* * * * *